United States Patent
Alper et al.

(10) Patent No.: US 8,025,904 B2
(45) Date of Patent: Sep. 27, 2011

(54) METHOD FOR CONTROLLING FIRE ANTS

(75) Inventors: Edward A. Alper, Houston, TX (US); Dennis M. Hoy, League City, TX (US)

(73) Assignee: STB Company, Houston, TX (US)

( * ) Notice: Subject to any disclaimer, the term of this patent is extended or adjusted under 35 U.S.C. 154(b) by 744 days.

(21) Appl. No.: 12/143,232

(22) Filed: Jun. 20, 2008

(65) Prior Publication Data

US 2009/0017134 A1    Jan. 15, 2009

Related U.S. Application Data

(60) Provisional application No. 60/945,146, filed on Jun. 20, 2007.

(51) Int. Cl.
*A01N 59/16* (2006.01)
*A01N 25/00* (2006.01)
*A61K 33/38* (2006.01)

(52) U.S. Cl. ............... 424/618; 424/405; 424/617
(58) Field of Classification Search ............ 424/405, 424/617–618
See application file for complete search history.

(56) References Cited

FOREIGN PATENT DOCUMENTS

KR    10-2006-0093994 A * 8/2006

* cited by examiner

*Primary Examiner* — Johann Richter
*Assistant Examiner* — Daniel L Branson
(74) *Attorney, Agent, or Firm* — Polsinelli Shughart PC

(57) ABSTRACT

A method for controlling fire ants is described, which includes applying a silver-containing composition to an area infested by fire ants or threatened by an infestation. The composition is applied to the area and reduces or eliminates the colony within a period of about two to four weeks and prevents fire ant re-infestation for a period of about six months to one year.

24 Claims, No Drawings

METHOD FOR CONTROLLING FIRE ANTS

CROSS REFERENCE TO RELATED APPLICATIONS

This application claims the benefit of U.S. provisional patent application No. 60/945,146 filed Jun. 20, 2007, the disclosure of which is herein incorporated by reference in its entirety.

GOVERNMENTAL RIGHTS

Not applicable.

INCORPORATION-BY-REFERENCE OF MATERIAL SUBMITTED ON A COMPACT DISC

Not applicable.

BACKGROUND OF THE INVENTION

The present teachings relate to methods for controlling insect pests.

Fire ants are known as pests across the globe and comprise almost 300 different known species of stinging ants. Most fire ant species are not a serious threat to humans and of the few species that are, most are controlled by natural forces such as parasites, predators and natural competition from other ant species. The species known as the red imported fire ant (*Solenopsis invicta*, also referred to as "RIFA") originated in South America and was inadvertently imported into the southern United States in 1929. Since then, in the absence of its natural predators, parasites and competitors, *S. invicta* has spread from coastal areas of Alabama to infest large parts of the southern U.S. Farmers and homeowners consider them a serious pest, and more recently they have spread to parts of Asia and Australia.

Fire ants feed primarily on young plants and germinating seeds and can cause significant agricultural damage, particularly to grain, fruit, nut and root crops. They occasionally eat other insects such as crickets, and may attack small animals and can kill them. They nest in soil and their large mounding nests have been linked to the decline of ground nesting birds such as the Bobwhite Quail. Although typically not a serious health threat, the sting of the fire ant can be quite painful and the discomfort is multiplied when, as often happens, the victim is attacked by multiple ants and suffers repeated stings. Sting sites are at risk of infection and scarring. Anaphylaxis is a known risk for certain individuals with heightened immunologic sensitivity to fire ant venom.

Individual mound treatment and broadcast treatment are two approaches to fire ant control using insecticides such as carbaryl, diazinon, and dursban, or an insect growth regulator. Both methods are limited primarily by the requirement that the active compound make direct and sometimes lasting contact with the colony ants and particularly the queen. Individual mound treatment is limited by the fact that the queen is sometimes too deep within the colony to be contacted by the active compound. Care must be taken not to disturb the mound prior to application of the drench. A disturbance will alert the colony and the queen may be taken deeper into the mound. In addition, application of insecticidal surface dusts or granules have a limited effect on a colony if they are not watered in. Dissolved granules must come into direct contact with the ants to have any effect. As in mound drenches, care must be taken not to disturb the colony prior to application. Some insecticides are intended as injectants. While injectants can be more effective than surface applications or mound drenches, they are also more expensive and can be dangerous if not handled properly.

Certain biological control methods have been tried. In the southern United States a species of phorid flies, a natural parasite of fire ants, have been introduced. Not all introductions have been successful, although the fly has been established successfully in some sites in every southeastern state. In Australia, fire ant colonies have been controlled with ground bait of food laced with contraceptive compounds that make the queens infertile. Some success has been obtained at the cost of instituting a necessarily highly organized, lengthy and costly national eradication campaign, including acquisition and analysis of satellite imaging data at a huge and ongoing financial cost. Moreover, broadcasting baits are limited by a slow time course of action, lack of specificity to fire ants, influence of temperature on ant retrieval of the bait, and the fact that the baits dissolve in water and become irretrievable by fire ants. A need thus remains for inexpensive, easy to use and effective methods for controlling fire ant infestations.

BRIEF SUMMARY OF THE INVENTION

In one aspect, the present teachings provide a method for repelling fire ants from an infested area by applying to the area a composition comprising silver in water. In one aspect the composition has a total silver content including silver ions and colloidal silver particles in water. Exemplary total silver content is about 0.5 PPM to about 35 PPM. In one aspect, the water is purified water. In another aspect, the composition is silver nitrate dissolved in water, which is for example deionized water. In an exemplary embodiment, the silver nitrate-based composition includes about 10 PPM to about 320 PPM silver nitrate. In one aspect of the method, the composition is applied to the infested area at a rate of about one gallon of the composition per about 400 ft2 of the infested area.

In another aspect, the present teachings provide a method for preventing a fire ant infestation comprising applying a composition comprising silver in water to an area in need of such prevention. In one aspect of the prevention method the composition has a total silver content including silver ion content and colloidal silver particles in water. Exemplary total silver content is about 0.5 PPM to about 35 PPM. In one aspect, the water is purified water. In another aspect, the composition is silver nitrate dissolved in water, which is for example deionized water. In an exemplary embodiment of the prevention method, the silver nitrate-based composition includes about 10 PPM to about 320 PPM silver nitrate. In one aspect of the prevention method, the composition is applied to the area in need of such prevention at a rate of about one gallon of the composition per about 400 ft$^2$ of the area.

In another aspect, the present teachings provide a kit for controlling or preventing a fire ant infestation in an area in need of such control or prevention, the kit including an amount of a composition comprising silver in water, a receptacle for receiving the amount of the composition, a spray attachment that attaches to the receptacle which is configured to couple with the spray attachment, and instructions for applying the composition to the area at a coverage rate sufficient to achieve a fire ant repellant effect. The composition can be a composition with a total silver content including both silver ions and colloidal silver particles in water. In an exemplary embodiment of the kit, such a composition has a total silver content of about 0.5 PPM to about 35 PPM and is made with purified water. In another aspect, the composition is made of silver nitrate dissolved in water. In an exemplary embodiment, the water is deionized water. The silver nitrate concentration is for example 10 PPM to about 320 PPM silver nitrate. In one embodiment, the kit instructions include instructions to apply the composition to the area at a rate of about one gallon of the composition per about 400 ft$^2$ of the area.

These and other features, aspects and advantages of the present teachings will become better understood with reference to the following description, examples and appended claims.

DETAILED DESCRIPTION OF THE INVENTION

Four species of fire ants are currently found within the contiguous southeastern United States. The tropical fire ant, *Solenopsis geminata* Fabricius, and the southern fire ant, *S. xyloni* McCook, are considered native to the area. Two imported species of fire ants were introduced into the United States from South America at the port of Mobile, Ala. The black imported fire ant, *Solenopsis richteri* Forel, arrived sometime around 1918 and the red imported fire ant, *Solenopsis invicta* Buren, in the late 1930's. The presence of imported fire ants in the United States was first reported in 1929 by Loding. Both species probably came to the port in soil used as ballast in cargo ships. In the years preceding the arrival of the *S. invicta*, the red imported fire ant, the black imported fire ant slowly spread into adjacent counties in Alabama and Florida. Since its introduction, the *S. invicta*, which is a much more aggressive species than *S. richteri*, has spread quickly. By the time of the first official survey carried out by the USDA in 1953, imported fire ants had invaded 102 counties in 10 states. Today, *S. invicta* has spread throughout the southeastern United States and Puerto Rico replacing the two native species and *S. richteri*. Currently, *S. richteri* is found only in extreme northeast Mississippi, northwest Alabama and a few southern counties in Tennessee. Nevertheless, although *S. invicta* currently presents the greatest pest control challenge in the U.S. and abroad, infestations of any species of imported fire ant can be locally devastating and costly.

The invention is based in part on the surprising discovery that application of a silver-containing composition to an area infested by fire ants repels the ants from the area and the repellant effect is maintained for a period of several months following application. In particular, the inventors have discovered that simple compositions containing silver in the form of silver particles and ions, or as silver nitrate dissolved in water are effective repellants of fire ants and their entire colonies. The invention provides an improvement over commonly used methods for fire ant control such as individual mound treatment and broadcast treatment, the effectiveness of which are limited as described elsewhere herein. The novel method described herein differs in its basic approach to the problem of fire ant infestation by apparently impacting the fire ants indirectly. Instead of killing or incapacitating the ants, the ants in a targeted colony are forced to migrate to a location away from the area treated with the silver-containing composition. Without being bound to particular theory, it is believed that application of the silver-containing composition creates highly unfavorable living conditions for the fire ants by reducing or eliminating their food supply, in particular by negatively impacting the growth or quality of fungi and bacteria in the soil. In any case, the inventors have shown that in response to application of the silver compositions as described herein, fire ant colonies either completely relocate to an untreated area, or the size of the colony is substantially reduced. It is believed that the inventors' results are applicable to the control of other insect pests for which fungi or bacteria are a major food source.

A composition for use according to the methods of the present invention may be made according to one of two exemplary formulations. In one embodiment, a composition containing silver particles and ions in water is used. In a second embodiment, a solution of silver nitrate in water is used. Silver concentration is most frequently reported as milligrams per liter (mg/L) or parts-per-million (PPM), which are numerically the same.

An exemplary embodiment of the method thus involves application of a composition containing particle and ionic silver in water. The phrase "particle and ionic silver" is intended to encompass any combination of particle silver and ionic silver varying from a combination of 100% ionic silver and 0% silver particles, to a combination of 0% ionic silver and 100% silver particles, inclusive. A suitable composition of particle and ionic silver is simply prepared in purified water using the electrolysis method. Municipal water is cleaned of impurities by reverse osmosis to a level of about 0 to about 7 TDS (Total Dissolved Solids) and then silver particles and ions are introduced into the water by running a low current/low DC voltage through a submerged silver/stainless steel electrode pair for a period of time adequate to obtain a composition containing about 0.5 PPM to about 35 PPM silver in the form of ionic silver and silver particles. Electrolysis methods for making such composition are simple and inexpensive and well known in chemistry and manufacturing For example, to make 1 gallon of a suitable silver composition containing particle and ionic silver, 12 pairs of silver/stainless steel cartridges are placed in 1 gallon of purified water, coupled to a power source of 2 to 6 volts and thus configured to provide a total current of 0.06 amps (or 0.005 amps per cartridge). The current is run for a period of about 10 minutes to produce a total silver content of 4 PPM. As is generally well known with electrolytic methods of production, the time required to produce a solution having a suitable total silver content (about 0.5 PPM to about 35 PPM) will vary with the amount of water, the number of cartridges, and the voltage and current applied. Alternatively, suitable silver particle and ionic compositions include any commonly commercially available "colloidal silver solutions" having total silver concentrations of about 0.5 PPM to about 35 PPM. Typically such products are sold as "colloidal silver" and described as solutions although they are more correctly "ionic silver solutions" containing about 90% ionic silver in solution and about 10% silver particles in colloidal suspension. Any such commercially available solutions may be used according to the methods of the present disclosure, and for the purposes of the present disclosure, the term "silver particles in colloidal form" or "colloidal silver" is intended to refer to any such silver solution containing both silver ions in solution and silver particles in colloidal suspension.

In a second embodiment, a suitable composition is prepared using readily commercially available silver nitrate (AgNO$_3$) crystals, dissolved in deionized water. In an exemplary embodiment, the silver nitrate concentration is about 10 PPM to about 320 PPM.

Methods for determining total silver in a solution are known and include for example the use of Atomic Absorption Spectrophotometers (MS), which have a minimum detection limit in the parts-per-billion range. AAS's such as the Perkin-Elmer Model 3030B Flame MS are now commonly used in analytical laboratories. Calibration of the AAS is performed using commonly commercially available standard silver dilutions of, for example, 100 PPM and 1000 PPM having an accuracy of 0.3%. Total silver concentration is determined according to manufacturer's recommendations.

Methods for applying liquids to a surface or area are generally well known and any method can be used that is reasonably well suited to applying about 1 gallon of solution per about 400 ft$^2$ without requiring an excessive amount of time and effort. Exemplary application methods are those capable of obtaining substantially uniform coverage of about 400 ft$^2$ using about 1 gallon of the solution and include methods such as spraying and sprinkling. However, other application methods suitable for application of liquids to a surface area can be used and include for example misting and bulk flow delivery. Bulk flow delivery, for example through a conduit such as a hose leading from a reservoir of the solution may be well suited to spot treatment of heavily infested areas. Spray application can be performed using any type of readily commercially available sprayer reasonably sized considering the total area needing coverage and the amount of solution that is to be applied.

A kit for controlling or preventing fire ant infestations is also provided. The kit conveniently provides, for example, off-the-shelf ability to practice the disclosed methods. The kit includes for example an amount of a silver containing composition as described herein, a receptacle such as a one-gallon container for holding the silver containing composition, a spray attachment or other liquid delivery or application device that couples to the receptacle, and printed instructions that explain the desired coverage rate for achieving the demonstrated repellant or preventative effect with respect to fire ants. For example, the instructions include the instruction to apply about one gallon of the composition to about 400 ft$^2$ of area to be treated. An exemplary kit includes packaging materials such as box, bag, blister pack or the like that conveniently receives and holds all elements of the kit.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

EXAMPLES

The following examples illustrate various iterations of the invention.

Example 1

Silver Nitrate Solution

A solution of silver nitrate (AgNO$_3$) was prepared by dissolving silver nitrate crystals (99.995% purity) in pure deionized water with a level of 0 TDS. Various concentrations of silver nitrate solution were made having a silver nitrate concentration in the range of 10 to 320 PPM.

Example 2

Particle and Ionic Silver Solutions

Particle and ionic silver solutions were prepared by the electrolysis method to produce silver particle and ionic solutions having various total silver concentrations from 0.5 to 35 PPM.

Example 3

Tests

Several different concentrations of both types of silver solutions were tested. Solutions were applied at a rate of one (1) gallon of solution per 400 ft$^2$ to grass areas infested by active fire ant mounds of several different sizes ranging from 2 inches to 2 feet in diameter using a commercial sprayer. Testing was performed at different times of day and during a range of weather conditions in the Houston, Tex. area.

Both types of the silver solution at all concentrations tested were tested independently with comparable results. Application of either type of solution reduced activity in fire ant mounds so that they become almost completely inactive. The time period over which ant activity decreased varied with the strength of the solution, the time of day of application and weather condition. Stable levels of inactivity were achieved over a period of weeks following single applications of each type of solution to moist soil in early spring (late February to mid-March). The most rapidly effective application was made around sunset in a freshly mowed test area that had been cleared of leaves and debris and stable reduction in activity was achieved within two (2) weeks. Results developed more slowly over a period of four (4) weeks when solution was applied to an unmowed tested area that was covered with debris around midday, or around sunset but during or just prior to heavy rain.

Several tests of each solution at different concentrations were conducted over fifteen (15) months. In all cases after an initial reaction period varying from about 2 to about 4 weeks during which fire ant activity steadily decreased, the treated areas were then free of fire ant mounds for approximately six (6) months to one (1) year. A second application of solution to the same mounds about one year after the initial treatment achieved the repellant result within a shorter period of about 1 to 2 weeks. After the initial application, the tested areas were regularly maintained (mowed and cleaned of debris).

These tests of the subject solutions were conducted with respect to fire ants, but it is believed that similar results can be achieved for other insect pests for which fungi or bacteria are a major food source.

Example 4

Toxicity

Additional laboratory tests were conducted in September/October of 2007 to examine the toxicity of the silver compositions. Laboratory-maintained fire ant colonies at Texas A&M University were provided with drinking water containing particle and ionic silver with a total silver content of 6 PPM for a period of one (1) month. No negative health effects were observed on the fire ant colonies in the lab environment.

Example 5

Effects on Soil

Additional tests were conducted in February/March of 2008 at the University of Houston Environmental Engineering laboratory with respect to effects on typical soil samples. Testing with both solutions having varying silver content showed that application of either silver-containing composition to typical soil decreased or eliminated a large variety of fungi and bacteria in the soil.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which modifications do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A method for repelling fire ants from an infested area comprising applying to the area a composition comprising silver in water.

2. A method according to claim 1 wherein the composition has a total silver content comprising silver ions and colloidal silver particles in water.

3. A method according to claim 2 wherein the total silver content is about 0.5 PPM to about 35 PPM.

4. A method according to claim 2 wherein the composition comprises purified water.

5. A method according to claim 1 wherein the composition comprises silver nitrate dissolved in water.

6. A method according to claim 5 wherein the water is deionized water.

7. A method according to claim 5 wherein the composition comprises about 10 PPM to about 320 PPM silver nitrate.

8. A method according to claim 1 further comprising applying the composition to the infested area at a rate of about one gallon of the composition per about 400 ft$^2$ of the infested area.

9. A method for preventing a fire ant infestation comprising applying a composition comprising silver in water to an area in need of such prevention.

10. A method according to claim 9 wherein the composition has a total silver content comprising silver ions and colloidal silver particles in water.

11. A method according to claim 10 wherein the total silver content is about 0.5 PPM to about 35 PPM.

12. A method according to claim 10 wherein the composition comprises purified water.

13. A method according to claim 9 wherein the composition comprises silver nitrate dissolved in water.

14. A method according to claim 13 wherein the water is deionized water.

15. A method according to claim 13 wherein the composition comprises about 10 PPM to about 320 PPM silver nitrate.

16. A method according to claim 9 further comprising applying the composition to the area in need of such prevention by spraying at a rate of about one gallon of the composition per about 400 ft$^2$ of the area.

17. A kit for controlling or preventing a fire ant infestation in an area in need of such control or prevention, the kit comprising: an amount of a composition comprising silver in water; a receptacle for receiving the amount of the composition, the receptacle having an opening configured to couple with a spray attachment; instructions for applying the composition to the area at a coverage rate sufficient to achieve a fire ant repellant effect.

18. A kit according to claim 17 wherein the composition has a total silver content comprising silver ions and colloidal silver particles in water.

19. A kit according to claim 18 wherein the total silver content is about 0.5 PPM to about 35 PPM.

20. A kit according to claim 18 wherein the composition comprises purified water.

21. A kit according to claim 17 wherein the composition comprises silver nitrate dissolved in water.

22. A kit according to claim 21 wherein the water is deionized water.

23. A kit according to claim 21 wherein the composition comprises about 10 PPM to about 320 PPM silver nitrate.

24. A kit according to claim 17 wherein the instructions comprise instructions to apply the composition to the area at a rate of about one gallon of the composition per about 400 ft$^2$ of the area.

* * * * *